United States Patent
Khoo et al.

(10) Patent No.: US 6,936,598 B2
(45) Date of Patent: Aug. 30, 2005

(54) COMPOSITION AND METHOD

(75) Inventors: Christina Khoo, Lawrence, KS (US);
Kathy Lynn Gross, Topeka, KS (US);
Glenn Gibson, Reading (GB)

(73) Assignee: Hill's Pet Nutrition, Inc., Topeka, KS (US)

(*) Notice: Subject to any disclaimer, the term of this patent is extended or adjusted under 35 U.S.C. 154(b) by 0 days.

(21) Appl. No.: 10/719,569

(22) Filed: Nov. 21, 2003

(65) Prior Publication Data

US 2005/0113334 A1 May 26, 2005

(51) Int. Cl.$^7$ .................. A61K 31/715; A61K 31/716; A23K 1/00
(52) U.S. Cl. .................. 514/54; 514/61; 536/123.1; 536/123.12; 426/635
(58) Field of Search .................. 514/54, 61; 536/123.1, 536/123.12; 426/635

(56) References Cited

U.S. PATENT DOCUMENTS

| | | | |
|---|---|---|---|
| 5,294,458 A | * | 3/1994 | Fujimori .................. 426/635 |
| 5,444,054 A | * | 8/1995 | Garleb et al. .................. 514/54 |
| 5,744,134 A | | 4/1998 | Paul |
| 5,939,309 A | | 8/1999 | Suwa et al. |
| 5,952,033 A | | 9/1999 | Anantharaman et al. |
| 5,968,569 A | | 10/1999 | Cavadini et al. |
| 6,051,260 A | | 4/2000 | Liska et al. |
| 6,156,355 A | | 12/2000 | Shields, Jr. et al. |
| 6,180,099 B1 | | 1/2001 | Paul |
| 6,197,361 B1 | | 3/2001 | Anantharaman et al. |
| 6,203,797 B1 | | 3/2001 | Perry |
| 6,241,983 B1 | | 6/2001 | Paul et al. |
| 6,270,811 B1 | | 8/2001 | Fregonese |
| 6,468,525 B1 | | 10/2002 | Watson et al. |
| 6,488,970 B1 | | 12/2002 | Hora |
| 6,544,568 B2 | | 4/2003 | De Simone |
| 6,592,863 B2 | | 7/2003 | Fuchs et al. |
| 6,706,287 B2 | | 3/2004 | Ranganathan et al. |
| 2002/0044988 A1 | | 4/2002 | Fuchs et al. |
| 2002/0127211 A1 | | 9/2002 | Brassart et al. |

OTHER PUBLICATIONS

Hara (Phytochemicals and Phytopharmaceuticals (2000), 214-221, Editor (3): Shahidi, Fereidoon; Ho, Chi-Tang) (Abstract Sent).*

Hara, "Antibacterial Actions of Tea Polyphenois and Their Practical Applications in Humans," Chapter 19, Food Research Laboratories, Mitsui Norin Company, Ltd., Fujieda, 426-01 Japan.

Loubinoux, et al., "Sulfate-reducing bacteria in human feces and their association with inflammatory bowel diseases, "*FEMS Microbiology Ecology* 40:197-112 (2002).

Gibson, et al., "Growth and activities of sulphate-reducing bacteria in gut contents of healthy subjects and patients with ulcerative colitis,"*FEMS Microbiology Ecology* 86:103-112 (1991).

Hirayama, "Novel physiological functions of oligosaccharides,"*Pure Appl. Chem.*, 74(7):1271-1279 (2002).

* cited by examiner

*Primary Examiner*—James O. Wilson
*Assistant Examiner*—Michael C. Henry
(74) *Attorney, Agent, or Firm*—James E. Davis; Wendell Ray Guffey

(57) ABSTRACT

A method for reducing the quantity of *Desulfovibrio* and/or *Helicobacter* spp. in the GI tract of a companion pet which comprises orally administering to the said pet a *Desulfovibrio* and/or *Helicobacter* spp. reducing quantity of a fiber or other component.

14 Claims, No Drawings

COMPOSITION AND METHOD

BACKGROUND OF THE INVENTION

Maintaining the well being of the GI tract of a mammal is a very desirable goal. Particularly relevant are inflammatory conditions of the GI tract. The *Desulfovibrio* spp. bacteria (including but not limited to *desulfuricans, intestinalis, vulgaris* etc.) are sulfate reducing bacteria that produce hydrogen sulfide which when released by the bacteria, can cause inflammation cells of the GI tract. *Helicobacter* bacteria (including but not limited to *heilmannii, felix, pylori, bizzozeronii, salomonis*) can cause ulcerations and inflammation of the cells of the stomach and upper intestines. Some signs of inflammation of the GI tract include acute or chronic diarrhea, soft stools, blood in stool, vomiting, poor nutrient digestion and absorption, weight loss and poor appetite. Diseases such as gastritis, enteritis, inflammatory bowel disease, ulcers, some types of cancer and others are known to have GI inflammation as a main component. Pathogenic bacteria such as *Desulfovibrio* spp., which reduce sulfate to sulfide, can also cause an increase in gas or stool odor due to increased levels of sulfide or other odiferous compounds in the stool.

We have now found that cats with inflammatory bowel disease (IBD) have a higher number of *Desulfovibrio* and/or *Helicobacter* spp. than normal, healthy cats. We have also found that Helicobacter was detectable in all cats with inflammatory bowel disease (IBD) whereas only 5/12 normal cats treated had detectable levels of helicobacter. We have also found that 45% of tested IBD cats had levels of bifidobacteria, a beneficial bacterial group, below standard detection levels, while 9% of normal, healthy cats had bifcdofacteria below standard detection levels.

SUMMARY OF THE INVENTION

In accordance with the invention, there is an orally edible food composition for use by a companion animal comprising an edible food composition in combination with a component which reduces the levels of *Desulfovibrio* and/or *Helicobacter* spp. in the companion animal.

A further aspect of the invention is a method for reducing the level of *Desulfovibrio* and/or *Helicobacter* spp. in a companion pet which comprises orally administering the food of the invention.

DETAILED DESCRIPTION OF THE INVENTION

As stated previously, it has now been discovered that *Desulfovibrio* spp. are higher in cats with a GI tract inflammation disorder, IBD, than normal cats not having this disorder. Therefore, it would be beneficial to any companion pet having a higher level of *Desulfovibrio* and/or *Helicobacter* spp. with or without overt clinical signs of a disease or disorder generally accompanied by GI tract inflammation to have their levels reduced. Benefits can also be derived from preventing *Desulfovibrio* and/or *Helicobacter* spp. from rising, that is a preventive effect.

The bacteria can be reduced by active agents. These include antibacterial materials such as antibiotics, chemotherapeutics and the like. Surprisingly, fibers can also reduce levels of *Desulfovibrio* and/or *Helicobacter* spp. as well. Examples of such fibers include an oligosaccharide, a galactan, a beta glucan and mixtures thereof. Examples of oliosaccharides include xylooligosaccharide, galactooligosaccharide, fructooligosaccharide and the like. Examples of a beta glucan include yeast cell extract, sprouted barley, oat fiber, curdlan (polysaccharide from microbial fermentation), and the like. Examples of galactans include arabinogalactan, and the like. Preferably a polyphenol(s) can also be present with the active agent, particularly where the active agent is a fiber, and more particularly where the fiber is a galactan such as arabinogalactan. The polyphenol is generally of a structure having at least two phenols and more preferably is a flavonoid such as a taxifolin. Minimum quantities of the polyphenol in the composition are a minimum of about 0.01, 0.05 or 0.1 wt % as measured on a companion pet's daily diet. The maximum generally does not exceed about 2, 1, or 0.75 wt % as measured on a companion pet's daily diet, all weights dry matter basis.

An anti *Desulfovibrio* and/or *Helicobacter* spp. effective amount of component can be employed. An antibacterial agent such as an antibiotic or chemotherapeutic agent can be provided orally to the pet at a minimum of about 2 & 5 mg/kg of body weight. Maximums are generally no more than about 25, 50 mg/kg of body weight. With respect to a fiber, the minimum is about 0.1, 0.5, or 1.0 wt % and the maximum generally should not exceed about 5, 10, or 20 wt % as measured on a companion pet's daily diet, dry matter basis.

*Desulfovibrio* and/or *Helicobacter* spp. reduction can be effective in helping to manage diseases and conditions in a companion pet wherein GI tract inflammation is a main component. Examples of companions pets are dogs, cats, horses, and the like.

EXAMPLE

Showing Presence of Increased Level of Pathogenic Bacteria in IBD Cats

1. Protocol for Screening of Fecal Samples from Cats:

Fecal samples were collected from normal healthy cats and those cats diagnosed with IBD. The normal cats were maintained on Science Diet® Feline maintenance® dry while the cats with IBD were maintained on a therapeutic gastrointestinal diet. The fecal samples were frozen at −70° C. prior to analysis. For analysis, samples were mixed with phosphate buffer saline to a ratio of 1:10 (w/w), vortexed with glass beads and centrifuged to remove particulate matter. An aliquot of 375 $\mu$l sample was added to a tube containing 1.125 ml of 4% paraformaldehyde and left at 4° C. for 4–5 hours. The samples were centrifuged and washed twice in PBS, then mixed with 150 $\mu$l of filtered ethanol and stored at −20° C. prior to fluorescent in situ hybridization analysis (FISH for microbial enumeration). Genus specific 16S rRNA-targeted probes were synthesized and monolabelled at the 5' end with fluorescent dye to detect the bacteria of interest in the fermentation media. Total nucleic acid was stained to obtain the total cell counts. The data are expressed as $\log_{10}$ cells/g feces. FISH allows bacerial quantification of stored samples and includes both culturable and non-culturable diversity.

Results

TABLE 1

Log$_{10}$ of colony forming units of pathogenic bacteria in normal and IBD cats

|  |  | Normal | IBD |
|---|---|---|---|
| Desulfovibrio feces | cfu/g | 7.0 ± 2.5 | 7.7 ± 0.6 |
| Helicobacter feces | cfu/g | 2.9 ± 3.6 | 7.3 ± 0.6 |

These results show that cats with GI tract inflammation, specifically IBD, had an increased quantity of pathogenic bacteria present in the GI tract.

EXAMPLE 2

Invivo Effect of AG on Desulfovibrio in IBD and Normal Cats

2. Protocol for Feeding Study

Eleven (11) cats with IBD and 10 normal healthy cats were fed foods containing 1.0% beetpulp with 0.6% arabinogalactan extract from the Western larch tree. The extract was approximately 90 wt % arabino galactan and about 4 wt % polyphenols, the predominant polyphenol being taxifolin, the remainder being moisture, all on a dry matter basis for two weeks. Following this, the cats were switched to food containing 1.5% beetpulp alone. Fecal samples were collected on days 0, day 14 and day 28. The samples were prepared as follows for FISH analysis: To freeze each fecal sample, 5 g of feces was suspended in anaerobic phosphate buffered saline (PBS) at pH7.3 in a sterile bag or plastic container to give a final concentration of 10% (45 ml for 5 g). The slurry was homogenized/mixed in the bag to avoid contamination. A different container was used for each sample. 5 ml of the slurry was mixed with an equal amount of glycerol to give a 50:50 mix which was frozen for analysis by FISH.

Results:

Thirteen (13) complete sets of fecal samples were obtained. When the cats were on food containing 0.6% AG extract, 4/13 cats had decreased Desulfovibiro spp. of 0.3 log units and above. 8/13 cats had small decreases or no change in the levels of Desulfovibrio spp. while only 1/13 cats had an increase in Desulfovibrio spp. When the cats were switched to food without AG, 10/13 cats had increased levels of Desulfovibrio spp. of 0.3 log units and above, 2/13 cats had no change and only 1/13 cats had decreased levels of Desulfovibrio spp.

The results show that AG extract was able to prevent an increase in Desulfovibrio spp. in most of the cats and tended to decrease in some of the cats. This was at the level that was fed compared to beetpulp, which tended to cause an increase in Desulfovibrio spp. in most of the cats.

EXAMPLE 3

In Vitro Experiment Showing that Various Fibers Decreased Levels of Desulfovibrio spp.

Fermentation vessels containing anaerobic phosphate buffered medium were prepared and 1 ml canine fecal inoculum (10% w/v fecal sample to buffer) added. The composition of the media was as described in Sunvold G D, Hussein H S, Fahey G C, Merchen N R, and Reinhart G A (1995), In vitro fermentation of selected fiber sources by dogs fecal inoculum and in vivo digestion and metabolism of fiber supplemental diets. J. Animal Sci. 73:1099–1109 (1995). Fermentations were carried out at 39° C. Experiments were conducted in a blind-coded manner with different fibers. After 8 hours incubation, 1 ml culture fluid was removed. An aliquot of this was prepared for FISH. After 8 hours, 1 ml of culture fluid was removed and mixed with 4% paraformaldehyde in PBS and fixed for FISH. Genus specific 16SrRNA-targeted probes were synthesized and mono-labelled at the 5" end with fluorescent dye to detect bacteria of interest in the fermentation media. Total nucleic acid was stained to obtain total microbial counts. The results showed that several different types of fibers were able to decrease the growth of Desulfovibrio spp. by 0.5 to 1.0 log units during the 8 hour fermentation (see Table 2).

TABLE 2

Numbers of Desulfovibrio spp. after 8 hour incubation (log cfu/ml of fecal inoculum).

|  | Log$_{10}$ CFU AT 0 HOUR | LOG$_{10}$ CFU AT 8 HOUR |
|---|---|---|
| Arabinogalactan | 7.5 ± 0.3 | 6.4 ± 1.0 |
| Xylooligosaccharide | 7.2 ± 0.4 | 6.8 ± 0.9 |
| Galacto-oligosaccharide | 7.0 ± 1.0 | 6.8 ± 0.9 |
| Fructooligosaccharide | 6.9 ± 1.0 | 6.3 ± 0.8 |
| Inulin | 7.3 ± 0.2 | 6.4 ± 1.0 |
| Sprouted barley | 6.8 ± 0.9 | 5.8 ± 0.0 |

SUMMARY

Therefore, we have shown both in vitro and in vivo that AG decreased the level of Desulfovibrio spp.

What is claimed is:

1. A method for reducing the quantity of Desulfovibrio and/or Helicobacter spp. in the GI tract of a companion pet which comprises orally administering to the said pet a Desulfovibrio and/or Helicobacter spp. reducing quantity of a fiber selected from the group consisting of an oligosaccharide, a galactan, a beta glucan and a mixture thereof, wherein said oligosaccharide is a galactooligosaccharide.

2. The method in accordance with claim 1 wherein the companion pet is in need of said administration.

3. The method in accordance with claim 2 wherein the companion pet is a dog or cat.

4. The method in accordance with claim 3 wherein the dog or cat has GI tract inflammation.

5. The method in accordance with claim 4 wherein the fiber is selected from the group consisting of arabinogalactan, galactooligosaccharide, inulin, sprouted barley and a mixture thereof.

6. The method in accordance with claim 1 wherein a polyphenol is also present.

7. A method for treating GI tract inflammation in a companion pet having an elevated level of Desulfovibrio and/or Helicobacter spp. in the GI tract comprising orally administering a Desulfovibrio and/or Helicobacter spp. reducing effective amount of a fiber selected from the group consisting of an oligosaccharide, a galactan, a beta glucan and a mixture thereof, wherein said oligosaccharide is a galactooligosaccharide.

8. The method in accordance with claim 7 wherein a polyphenol is also present.

9. A method for treating GI tract inflammation in a companion pet having an elevated level of *Desulfovibrio* and/or *Helicobacter* spp. in the GI tract comprising orally administering a *Desulfovibrio* reducing effective amount of a component which reduces the quantity of *Desulfovibrio* and/or *Helicobacter* spp. in the GI tract wherein said component is selected from the group consisting of an oligosaccharide, a galactan, a beta glucan and a mixture thereof, and wherein said oligosaccharide is a galactooligosaccharide.

10. A method for reducing an odor selected from the group consisting of intestinal gas odor, stool odor and any mixture thereof in a companion pet having an elevated level of *Desulfovibrio* and/or *Helicobacter* spp. which comprises orally administering a *Desulfovibrio* and/or *Helicobacter* spp. reducing effective amount of a component which reduces the quantity of *Desulfovibrio* and/or *Helicobacter* spp. in the GI tract, wherein said component is selected from the group consisting of an oligosaccharide, a galactan, a beta glucan and a mixture thereof, and wherein said oligosaccharide is a galactooligosaccharide.

11. The method of claim 10, wherein said component is said galactan, said beta glucan or a mixture thereof.

12. The method of claim 1, wherein said fiber is selected from the group consisting of said galactan, said beta glucan and a mixture thereof.

13. The method of claim 12, wherein said fiber is said galactan.

14. The method of claim 12, wherein said fiber is said beta glucan.

* * * * *